US009968557B1

United States Patent
(12) United States Patent
Sachdeva et al.

(10) Patent No.: US 9,968,557 B1
(45) Date of Patent: May 15, 2018

(54) METHOD OF PREPARING MODIFIED MULTILAYERED MICROSTRUCTURES WITH ENHANCED ORAL BIOAVAILABILITY

(71) Applicant: Florida A&M University, Tallahassee, FL (US)

(72) Inventors: Mandip Sachdeva, Tallahassee, FL (US); Apurva Patel, Longwood, FL (US)

(73) Assignee: Florida A&M University, Tallahassee, FL (US)

( * ) Notice: Subject to any disclaimer, the term of this patent is extended or adjusted under 35 U.S.C. 154(b) by 156 days.

(21) Appl. No.: 15/046,087

(22) Filed: Feb. 17, 2016

Related U.S. Application Data

(63) Continuation-in-part of application No. 13/368,993, filed on Feb. 8, 2012.

(60) Provisional application No. 61/561,840, filed on Nov. 19, 2011, provisional application No. 61/440,977, filed on Feb. 9, 2011.

(51) Int. Cl.
*A61K 9/16* (2006.01)
*A61K 31/404* (2006.01)

(52) U.S. Cl.
CPC ............ *A61K 9/1682* (2013.01); *A61K 9/167* (2013.01); *A61K 9/1617* (2013.01); *A61K 31/404* (2013.01)

(58) Field of Classification Search
CPC . B05B 17/06; B05B 17/0607; B05B 17/0615; B05B 17/0623; B05B 17/063; A61K 9/1682; A61K 9/1617; A61K 9/167; A61K 31/404
USPC ...... 239/102.1, 102.2, 407, 412, 413, 416.4, 239/416.5, 417.3, 417.5, 423, 424, 4, 8, 239/10
See application file for complete search history.

(56) References Cited

U.S. PATENT DOCUMENTS

| | | | |
|---|---|---|---|
| 4,352,459 | A | 10/1982 | Berger et al. |
| 6,702,195 | B2 | 3/2004 | Trabold |
| 7,378,110 | B2 | 5/2008 | Truong-Le et al. |
| 7,594,614 | B2 | 9/2009 | Vijay et al. |
| 7,670,579 | B2 | 3/2010 | Chow et al. |

(Continued)

OTHER PUBLICATIONS

Yoo et al., Novel self-nanoemulsifying drug delivery system for enhanced solubility and dissolution of lutein, Arch Pharm Rse, Mar. 2010; vol. 33 (Issue3):417-26.

(Continued)

*Primary Examiner* — Christopher Kim
(74) *Attorney, Agent, or Firm* — Nilay J. Choksi; Smith & Hopen, P.A.

(57) ABSTRACT

A dual channel spray gun, and method of use thereof, for fabricating nanostructures including a pharmaceutical/therapeutic agent having enhanced oral bioavailability. The nanostructures are a mixture of at least two (2) solutions/media substantially equally distributed as desired. The spray gun device uses gas pressure and/or two ultrasonicators to simultaneously prepare two solution systems for subsequent mixture and atomization. The gas pressure and frequencies of the ultrasonicators are adjustable for each channel of the spray gun. In operation, the spray gun is used to prepare microstructures that, for example, contain at least one active pharmaceutical agent in one solution system and excipients, such as coating or bioadhesives, in the other solution system. Any combination of solution systems is contemplated, such as both systems containing a pharmaceutical agent or both systems containing excipients.

16 Claims, 11 Drawing Sheets

(56) References Cited

U.S. PATENT DOCUMENTS

| | | | |
|---|---|---|---|
| 7,736,666 | B2 | 6/2010 | Holmberg et al. |
| 7,807,200 | B2 | 10/2010 | Lipp et al. |
| 7,815,933 | B2 | 10/2010 | Holmberg |
| 2005/0037073 | A1 | 2/2005 | Schwarz |

OTHER PUBLICATIONS

E. Toorisaka et al., An enteric-coated dry emulsion formulation for oral insulin delivery. Journal Controlled Release, Sep. 20, 2005; vol. 107 (Issue1):91-6.

Fernandez-Tarrio et al., Pluronic and Tetronic Copolymers with Polyglycolyzed Oils as Self-Emulsifying Drug Delivery Systems, AAPS PharmSciTech, 2008; vol. 9 (Issue 2):471-9.

Nekkanti et. al., Solid self-microemulsifying formulation for candesartan cilexetil, AAPS PharmSciTech, Mar. 2010; vol. 11 (Issue 1):9-17.

Rujivipat et al., Improved drug delivery to the lower intestinal tract with tablets compression-coated with enteric/nonenteric polymer powder blends, Eur J Pharm Biopharm, Sep. 22, 2010; PMID: 20868750, vol. 76: 486-92.

Rujivipat et al. Modified release from hydroxypropyl methylcellulose compression-coated tablets. Int J Pharm. Dec. 15, 2010; vol. 402 ( Issues 1-2):72-7. Epub Sep. 29, 2010.

Dalmoro et al., Enteric Micro-Particles for Targeted Oral Drug Delivery, AAPS PharmSciTech, Dec. 2010 PMID: 20931307, vol. 11 (No. 4):1500-07.

Hu et al., Continuous and scalable process for water-redispersible nanoformulation of poorly aqueous soluble APIs by antisolvent precipitation and spray-drying. Int J Pharm. Nov. 2010. vol. 404: 198-204.

Bowey et al., Systemic and mucosal delivery of drugs within polymeric microparticles produced by spray drying, BioDrugs. Dec. 1, 2010; vol. 24 (Issue 6):359-77.

Holzschuh et al., Identification and stability of a new bichalcone in Achyrocline satureioides spray dried powder. Pharmazie. Sep. 2010;65(9):650-6.

Cui et al., Self-microemulsifying drug delivery systems (SMEDDS) for improving in vitro dissolution and oral absorption of Pueraria lobata isoflavone. Drug Development Industrial Pharmacy. May 2005;31(4-5):349-56.

Yi et al., A new solid self-microemulsifying formulation prepared by spray-drying to improve the oral bioavailability of poorly water soluble drugs. European Journal Pharmacy and Biopharmaceutics. Oct. 2008; 70(2):439-44.

Yi et al., Controlled poorly soluble drug release from solid self-microemulsifying formulations with high viscosity hydroxypropylmethylcellulose. European Journal Pharmaceutical Sciences. 2008; 34(4-5):274-80.

J. Cui et al., Enhancement of oral absorption of curcumin by self-microemulsifying drug delivery systems, International Journal Pharmaceutics, Apr. 17, 2009; vol. 371(1-2):148-55.

R.P. Raffin et al., Enteric controlled-release pantoprazole-loaded microparticles prepared by using Eudragit S100 and poly(epsilon-caprolactone) blend, Pharmaceutical Development Technology, 2007; vol. 12(5):463-71.

Obeidat et al., Preparation and evaluation of Eudragit S 100 microspheres as pH-sensitive release preparations for piroxicam and theophylline using the emulsion-solvent evaporation method, Journal of Microencapsulation, Mar. 2006; vol. 23(Issue 2):195-202.

F F O Sousa et al., Development of a novel AMX-loaded PLGA/zein microsphere for root canal disinfection. Biomed Mater. Oct. 2010; vol. 5 (Issue 5):055008, 1-10.

M. Orlu et al., Design and evaluation of colon specific drug delivery system containing flurbiprofen microsponges. International Journal Pharmaceutics. Aug. 2, 2006; vol. 318(1-2):103-17.

V. Iannuccelli et al., Microparticulate polyelectrolyte complexes for gentamicin transport across intestinal epithelia. Drug Delivery, Aug. 21, 2011. vol. 18 (Issue 1): 26-37.

Abdalla et al., A new self-emulsifying drug delivery system (SEDDS) for poorly soluble drugs: characterization, dissolution, in vitro digestion and incorporation into solid pellets, Eur J Pharm Sci, Dec. 18, 2008; vol. 35 (Issue 5):457-64.

Patel et al., Evaluation of Spray BIO-Max DIM-P in Dogs for Oral Bioavailability and in Nu/nu Mice Bearing Othotopic/Metastatic Lung Topic Models for Anticancer Activity. Pharm Res. Jan. 2015: 1-9.

METHOD OF PREPARING MODIFIED MULTILAYERED MICROSTRUCTURES WITH ENHANCED ORAL BIOAVAILABILITY

CROSS-REFERENCE TO RELATED APPLICATIONS

This application is a continuation-in-part of and claims priority to U.S. Nonprovisional application Ser. No. 13/368,993, entitled "Dual Channel Spray Dryer and Modified Multilayered Microstructures for Oral Delivery by Use Thereof", filed on Feb. 8, 2012 by the same inventors, which claims priority to U.S. Provisional Application No. 61/561,840, entitled "Ultrasonic dual channel spray dried modified multilayered microstructures for oral delivery", filed on Nov. 19, 2011 by the same inventors, and to U.S. Provisional Application No. 61/440,977, entitled "Dual channel spray dried modified multilayered microstructures for oral delivery", filed on Feb. 9, 2011 by the same inventors, all of which are incorporated herein by reference in their entireties.

FEDERALLY SPONSORED RESEARCH OR DEVELOPMENT

This invention was made with Government support under Grant No. G12 RR003020 awarded by the National Institutes of Health. The government has certain rights in the invention

BACKGROUND OF THE INVENTION

1. Field of the Invention

This invention relates, generally, to multilayered microstructures containing one or more active pharmaceutical agents for oral delivery. More particularly, it relates to multilayered microstructures modified to enhance bioavailability of one or more pharmaceutical agents in different combinations.

2. Description of the Prior Art

About 50% of new active pharmaceutical agents have poor water solubility. Thus, the oral delivery of such drugs is frequently associated with low bioavailability. Oral administration presents a series of advantages, including high desirability in the treatment of pediatric patients. Oral delivery also avoids additional risks, and the pain and discomfort associated with injections. Furthermore, oral formulations are less expensive to produce, as they do not need to be manufactured under sterile conditions. The majority (about 84%) of the fifty most popular pharmaceutical products in the U.S. and European markets are given orally.

To overcome the problems associated with oral drug delivery, such as poor solubility, poor absorption, degradation in acidic stomach environment, etc., various formulation strategies have been exploited. These strategies include the use of surfactants, lipids, permeation enhancers, micronization, salt formation, cyclodextrins, nanoparticles, enteric coating, sustained release, controlled release, solid dispersions, freeze drying, spray drying and self-emulsifying drug delivery.

A conventional approach to enhancing oral bioavailability of is the utilization of lipid based drug delivery systems.

Self-emulsifying drug delivery systems (SEDDS) are a class of lipid based delivery systems and are comprised of oils, surfactants, solvents/co-solvents and surfactants, and are generally administered in a liquid dosage form or soft gelatin capsules, which have some disadvantages especially in the manufacturing process. However, solid self-emulsifying drug delivery systems (S-SEDDS), prepared by solidification of liquid/semi-solid self-emulsifying ingredients into powders, are also known. Spray drying facilitates the transformation of liquid or semi-solid formulations into solid particles which could subsequently be filled into hard gelatin capsules, sachets or compressed into tablets.

Dry emulsion technology resolves stability problems associated with classic emulsions (phase separation, contamination by microorganism, etc.) during storage and helps also avoid using harmful or toxic organic solvents. Spray drying has been widely used to produce polymeric microparticles for systemic delivery in order to control the delivery of drugs, vaccines, or genetic material that may exhibit poor pharmacokinetic profiles or pose toxicity concerns. Other than SEDDS and spray drying, enteric coating has been known to improve bioavailability of drugs that are absorbed in intestine.

However, with an increasing number of new active pharmaceutical agents, newer and improved techniques are needed to enhance bioavailability, efficiency and effectiveness of orally-delivered drugs, particularly anti-cancer drugs. It has been reported that oral delivery of many active pharmaceutical agents does not show effective concentrations in plasma. In addition, because of low bioavailability, the amount of active pharmaceutical agents required to achieve the desired effectiveness is higher in oral delivery than in traditional intravenous delivery.

Use of self-emulsifying drug delivery technique has also been reported (Yoo et al., Novel self-nanoemulsifying drug delivery system for enhanced solubility and dissolution of lutein. Arch Pharm Rse. 2010 March; 33(3):417-26; Abdalla et al., A new self-emulsifying drug delivery system (SEDDS) for poorly soluble drugs: characterization, dissolution, in vitro digestion and incorporation into solid pellets, Eur J Pharm Sci. (2008) Dec. 18; 35(5):457-64). Similarly, Fernandez-Terrio et al. report use of copolymers with polyglycolyzed oils as self-emulsifying drug delivery system (AAPS PharmSciTech (2008) 9(2):471-9). However, the utilization and effectiveness of this system was limited due to stability. Several researchers have shown modified system by making solid self-emulsifying drug delivery systems (Nekkanti et. al. Solid self-micro emulsifying formulation for candesartan cilexetil. AAPS PharmSciTech, (2010 March) 11(1):9-17).

Rujivipat et al. reported use of enteric coating for improved oral delivery where compressed enteric polymer coated formulation was used (Rujivipat et al. Improved drug delivery to the lower intestinal tract with tablets compression-coated with enteric/nonenteric polymer powder blend, Eur J Pharm Biopharm (2010 Sep. 22) PMID: 20868750). Also, Rujivipat et al. modified release from hydroxypropyl methylcellulose compression-coated tablets (Int J Pharm. 2010 Dec. 15; 402(1-2):72-7, Epub 2010 Sep. 29). Similarly, Dalmoro et al. also reported enteric coated microparticles for targeted oral drug delivery (AAPS PharmSciTech. 2010 Oct. 8. PMID: 20931307).

Further, recent studies report that use of spray drying for improved oral bioavailability was effective with different drugs showed effectiveness (Hu et al. Continuous and scalable process for water-redispersible nanoformulation of poorly aqueous soluble APIs by antisolvent precipitation and spray-drying, Int J Pharm, (2010 Nov. 5) PMID: 21056643; Bowey et al., Systemic and mucosal delivery of drugs within polymeric microparticles produced by spray drying, BioDrugs, (2010 Dec. 1) 24(6):359-77; Holzschuh et al., Identification and stability of a new bichalcone in *Achyrocline satureioides* spray dried powder, Pharmazie, (2010 September) 65(9):650-6).

Despite this advancement, the outcome and utility of these techniques were limited at least in part by the ability to orally deliver only one active pharmaceutical agent in enteric coated, self-emulsifying microparticles. Moreover, conventional spray guns allow only one process at a time, either spray drying or coating. Conventional spray guns also do not accommodate two different formulations in a single technique to give a final product. To do this, conventional spray guns, such as that found in U.S. Pat. No. 4,352,459, which is hereby incorporated by reference, must process a single formulation and reprocess that with a second formulation to produce the final result. This adds time, cost, resources, imprecision, etc. Additionally, effectiveness of oral delivery must still be increased, whether one active pharmaceutical agent is being delivered or multiple active pharmaceutical agents are being delivered. To date, no study has been reported for enteric-coated, self-emulsifying, multilayered microparticles containing one or more active pharmaceutical agents delivered orally.

Accordingly, what is needed is an oral delivery system for one or more active pharmaceutical agents having high efficiency, effectiveness and bioavailability. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions, or is known to be relevant to an attempt to solve any problem with which this specification is concerned.

SUMMARY OF THE INVENTION

The long-standing but heretofore unfulfilled need for improved and more effective oral delivery of one or more active pharmaceutical agents is now met by a new, useful and nonobvious invention.

The invention relates to the development and oral delivery of modified multilayered microstructures containing active pharmaceutical agent(s). The microstructures are modified by exposure to an ultrasonic, dual channel spray gun, or spray dryer. The spray dryer simultaneously dries the inner core or droplets embedded into the outer layer or matrix of one or more excipients within the multilayered microstructures. This drying enables various combinations of pharmaceutical formulations to enhance bioavailability of the one or more active pharmaceutical agents by enhanced absorption in the gastrointestinal tract of a patient in need thereof.

An embodiment of the current invention is a spray gun that can be used to simultaneously prepare and atomize two solutions to produce a spray. The spray gun comprises a first pump that receives a first solution and a second pump that receives a second solution. The first pump is connected to a first channel, and the second pump is connected to a second channel. A gas pump pressurizes the channels and forces the solutions to travel down their respective channels. The gas pump can have a pressure for the first channel that is different from the pressure for the second channel, so that each solution can be prepared at the same time. The solutions mix at the spray tip, and the resultant mixture is atomized to produce a spray.

The spray device may include two ultrasonicators, one connected to the first channel and the other connected to the second channel. The ultrasonicators each vibrate at set frequencies to further induce the solutions contained within the respective channels.

The gas pump may be a compressed air pump.

The spray tip may include a bore with a diameter of about 0.5 mm to about 0.8 mm.

In a separate embodiment, the current invention is a spray gun that can be used to simultaneously prepare and atomize two solutions to produce a spray. The spray gun comprises a first pump that receives a first solution and a second pump that receives a second solution. The first pump is connected to a first channel, and the second pump is connected to a second channel. The first channel is connected to a first sonicator that vibrates to force the solution to flow through the first channel. Similarly, the second channel is connected to a second sonicator that vibrates to force the solution to flow through the second channel. The first sonicator may be adjusted to vibrate at a different frequency than the second sonicator. After the solutions have passed through their respective channels, the solutions mix at the spray tip, and the resultant mixture is atomized to produce a spray.

The spray tip may include a bore with a diameter of about 0.5 mm to about 0.8 mm.

In a separate embodiment, the current invention is a method of preparing orally-deliverable microstructures that are modified for increase bioavailability. A first solution is pumped into a first channel of a spray gun, and a second solution is pumped into a second channel of the spray gun. A first sonicator, connected to the first channel, is activated, as is a second sonicator, connected to the second channel. The vibrations of the first and second sonicators force the first and second solutions, respectively, down the first and second channels, respectively, until the solutions reach the ends of the channels. The solutions are then mixed in the spray tip, which extends from the channels. The mixture is atomized and a spray outputted. The spray is heated, and the liquid phase of the spray evaporates, leaving behind a solid particulate containing the microstructures. The solid particulate is recovered.

The first solution may be a self-emulsifying drug delivery system.

The first and second sonicators may be activated at the same time to prepare the solutions simultaneously.

The first solution may contain at least one at least one active pharmaceutical agent. Further, the second solution may be a polymer solution containing excipients, or alternatively, the second solution may contain another active pharmaceutical agent. Further, if the second solution contains another active pharmaceutical agent, then the first and second solutions may contain excipients.

The active pharmaceutical agent may be DIM-P.

The vibration frequencies of the first and second sonicators may be individually adjusted upon their activations.

The vibration frequency of the spray tip may be adjusted upon its activation.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Certain embodiments of the present invention relate to oral delivery of modified multilayered microstructures containing one or more active pharmaceutical agents. Though the disclosure herein focuses on the oral delivery of drugs, it is also contemplated that the disclosed invention can be used in trans-dermal, ophthalmic, vaginal, and buccal cavity deliveries. Multilayered microstructures are prepared by spray drying via an ultrasonic dual channel spray system. This ultrasonic dual channel spray drying system is modified from conventional single channel where only one liquid may be spray dried. This modification allows spraying of two separate liquid systems containing one or more active pharmaceutical agents. Each channel or matrix may comprise an active pharmaceutical agent.

In the present invention, one or more lipids, polymers, surfactants, solubilizer and bulking agents are used to prepare multilayered microparticles. Lipids affect the oral bioavailability of drugs by changing their biopharmaceutical properties. More particularly, lipids increase dissolution rate and solubility in the intestinal fluid, protect the drug from chemical as well as enzymatic degradation, and formation of lipoproteins promoting lymphatic transport.

SEDDS are usually limited to liquid dosage forms because many excipients used in SEDDS are not solids at room temperature. S-SEDDS have shown to be advantageous for solid forms and are an effective alternative to liquid SEDDS. S-SEDDS focus on the incorporation of liquid/semisolid SE ingredients into powders/nanoparticles/microparticles by different solidification techniques, such as adsorpotions to solid carriers, spray drying, melt extrusion/extrusion spheronization, nanoparticles technology, and melt granulation.

Figure 1:
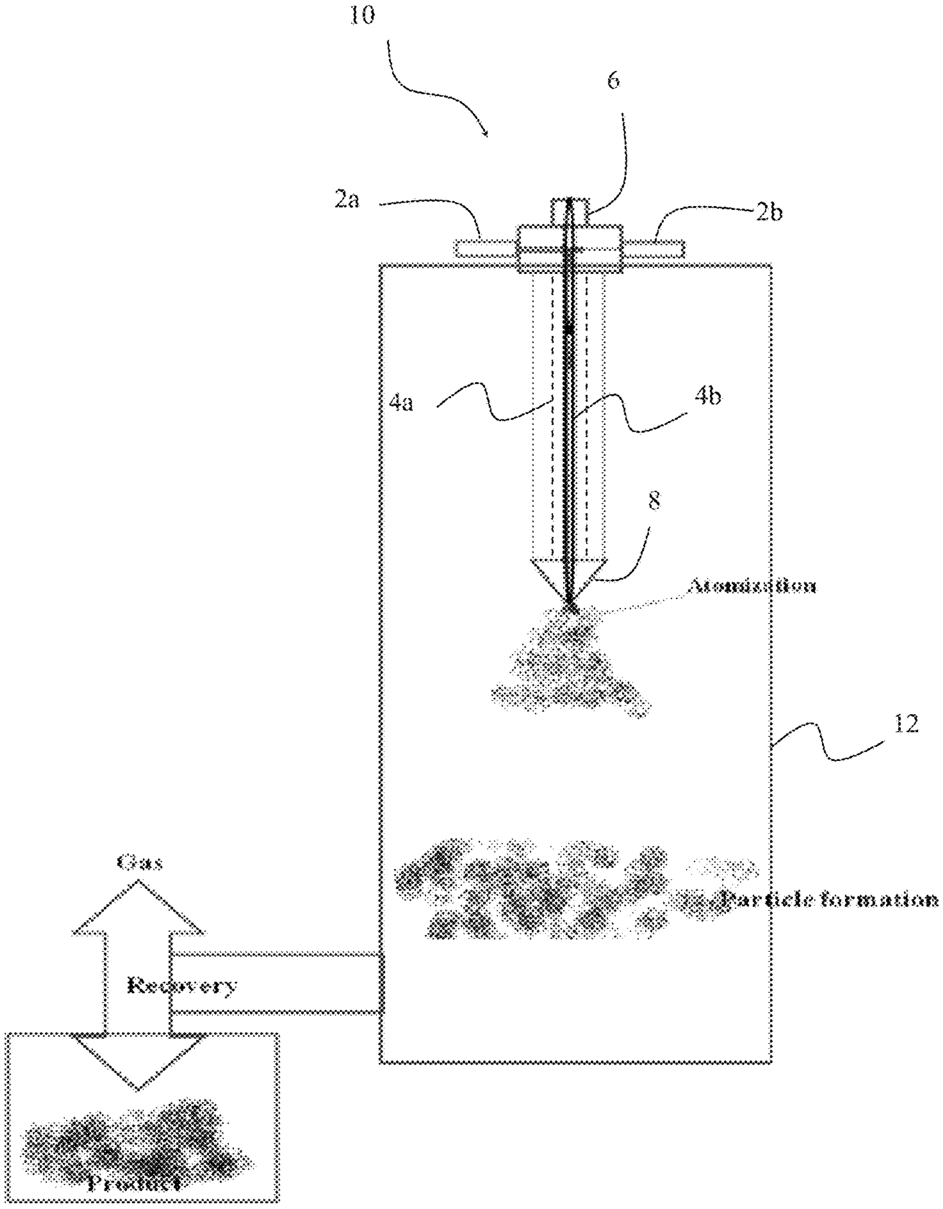
FIG. 1 depicts a schematic pathway for a dual channel spray system.
Figure 4:
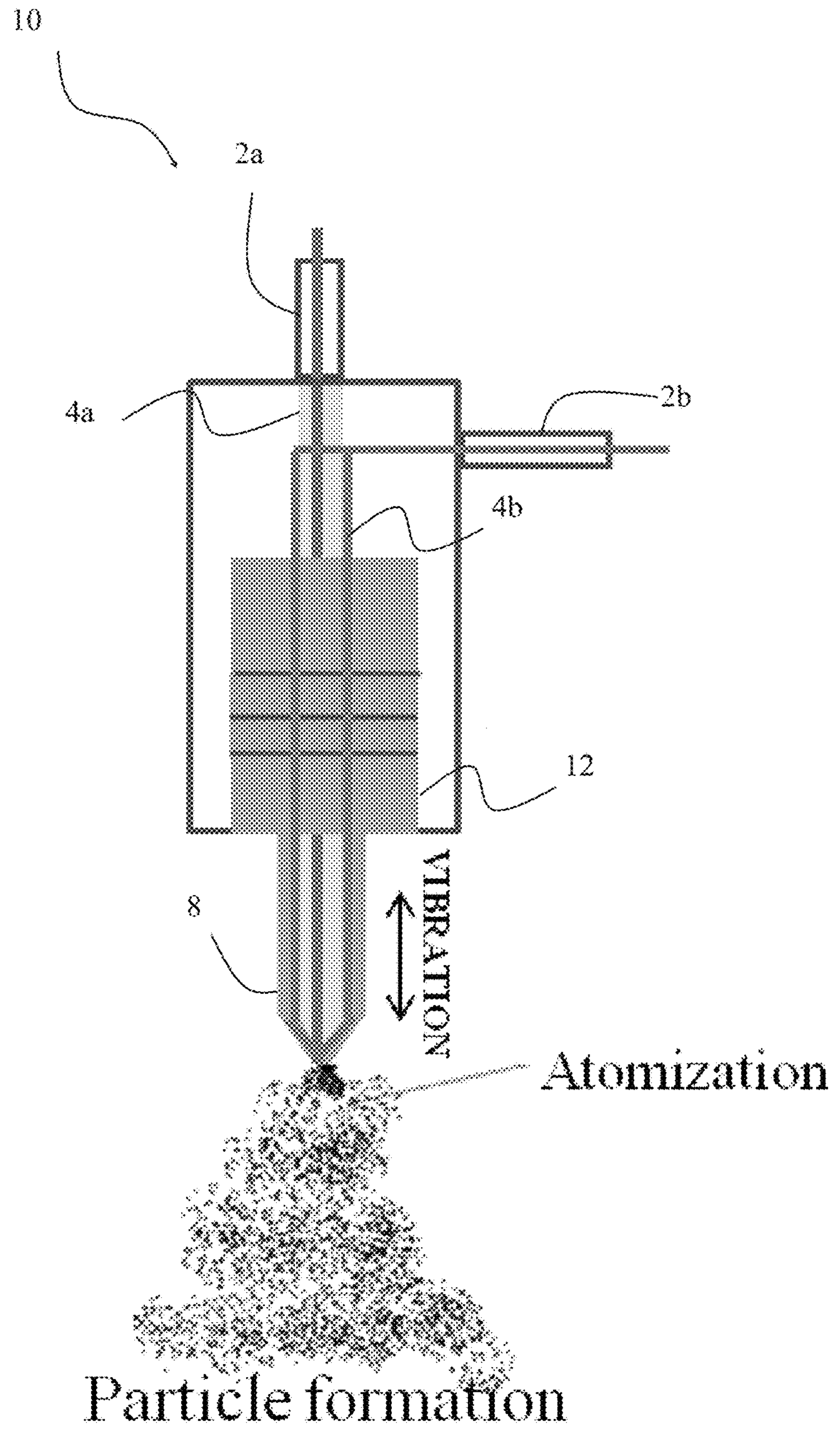
FIG. 4 depicts a schematic pathway for an ultrasonic dual channel spray system.
Figure 5:
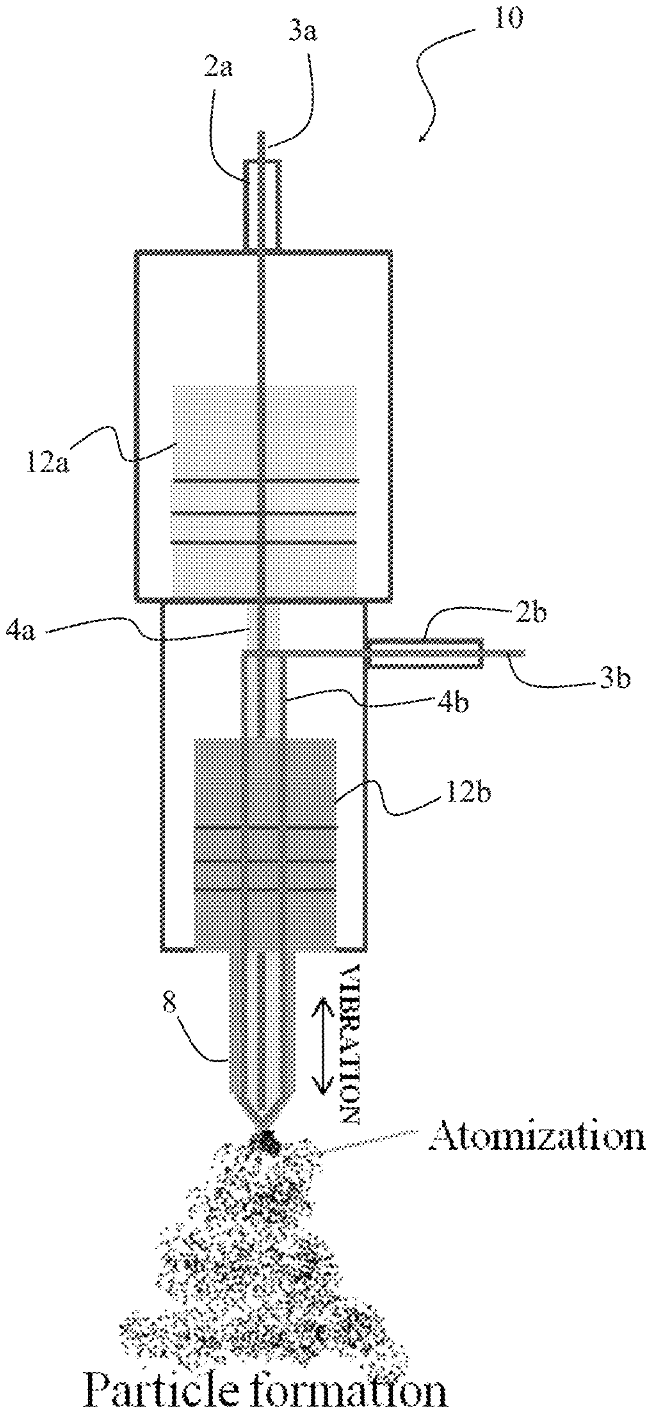
FIG. 5 depicts a schematic pathway for an ultrasonic dual channel spray system.

More particularly regarding spray drying, the multilayered microstructures can be prepared using a dual channel simultaneous spray drying system, such as one depicted in FIGS. 1, 4 and 5. The spray drying system may have ultrasonic capabilities.

The utilization of this system is not limited to enteric coated self-emulsifying microstructures. Other approaches include, but are not limited to, controlled release, immediate release, pulsatile release and bioadhesive control release.

The process of producing the microstructures includes the preparation of a formulation by mixing lipids, surfactants, drug, solid carriers, and solubilization of the mixture before spray drying. Spray drying itself involves atomization, drying, particle formation and recovery. The atomizer, the temperature, the most suitable airflow pattern and the drying chamber design are selected according to the drying characteristics of the product and powder specification.

The present invention comprises the oral delivery of one or more active pharmaceutical agents. The active pharmaceutical agents used in the current invention may include, but are not limited to, anti-inflammatory agents, anti-psoriatic agents, analgesic agents, anti-parasitic agents, anti-cancer agents, anti-bacterial agents, anti-fungal agents, anti-viral agents, immunomodulators, proteins and peptides, nucleosides, nucleotides, enzymes, hormones, vitamins, minerals and natural compounds used for treatment as well as diagnostic purpose.

The current invention comprises the dual chamber spray gun and the drugs that that result therefrom. Therapeutic ranging of a drug is based mainly on the drug's physicochemical properties, though other properties are considered as well. The active pharmaceutical agents used in certain embodiments of the present invention include lipophilic compounds (for treatment of cancer) with log P (partition co-efficient) greater than 4. The active pharmaceutical agents used may also include drugs with solubility and permeability issues in the gastrointestinal tract of a patient in need thereof. It is contemplated that the present invention may be applied to larger groups of active pharmaceutical agents as well.

The active pharmaceutical agents comprise small molecules, proteins and peptides, alone or in combination, with one or more small molecules, proteins and peptides, alone or in combination. One or more active pharmaceutical agents is delivered orally for systemic application, as well as local application throughout the gastrointestinal tract. In a preferred embodiment, one or more active pharmaceutical agents is delivered primarily to the intestine (i.e., duodenum, jejunum and colon).

I. DUAL CHANNEL SPRAY DRYER WITH ULTRASONIC SPRAY NOZZLE

FIGS. 1, 4 and 5 depict various embodiments of dual channel spray dryer, generally denoted by the reference numeral 10. Spray dryer 10 allows simultaneous pulsatile flow of two different liquid systems through pumps 2*a* and 2*b*. This enables use of SEDDS as a first liquid system through pump 2*a* and enteric coating system (e.g., polymer solutions) as a second liquid system through pump 2*b*. A user may then simultaneously generate microparticles with a uniform coating, thereby reducing process time, cost and resources. Dual channel spray dryer 10 can be used for any purpose that requires the combination of multiple solutions or systems. Examples include, but are not limited to, coating, bioadhesives, among other mixtures that require two solutions/systems to be separately prepared and subsequently combined. As such, any solution and/or any pharmaceutical agent can be used in the spray dryer to produce a more bioavailable drug or molecule.

Atomizer pumps 2*a*, 2*b*, and 6 (only in FIG. 1) have a flow-through design. Substrate, not shown, that is desired to be admixed into the final solution can be inserted into spray dryer or probe 10 and can travel into either channel 4*a* or 4*b* of probe 10. Typically substrate will be pumped into the same channel as the polymer solution. Liquid can then be pumped at the rear of spray dryer 10 through pump 2*a* or 2*b* and can travel down through channel 4*a* or 4*b* of spray dryer 10 until the liquid reaches vibrating tip 8. Once the liquid reaches tip portion 8 of nozzle 10, ultrasonic vibrations pulverize the liquid into ultra-fine particles for precise coating applications without the use of air pressure.

In an embodiment, as depicted in FIG. 1, pump 6 receives gas or compressed air, which is used to push solutions through channels 4*a*, 4*b* until the solutions reach tip 8. Pump 6 is in fluid communication with channel 4*a* and with channel 4*b* individually. Thus, gas pressure can be adjusted for channel 4*a* and channel 4*b*, depending on the needs of the resultant atomized droplets, so that each solution can be separately but simultaneously prepared. When the solutions have traveled down channels 4*a*, 4*b*, the solutions admix in tip 8 and are atomized into droplets. The droplets are then heated in heating chamber 12 to evaporate the liquid phase out of the droplets. Upon evaporation, particulate forms, gas is expelled, and the resultant microparticles (e.g., a powder) are recovered or collected.

In an embodiment, if gas pressure is not used to push solutions through channels 4*a*, 4*b*, the center of probe 10 may contain one or more generators, not shown, that can convert an electrical signal received from a conventional control system, not shown, to mechanical vibration. The control system determines how much electronic impulse is sent to the generators for conversion into mechanical vibration. This vibration determines frequency. This vibration can be amplified by the shape that forms tip 8 of probe 10 because tip 8 has a vibration that is reflected back towards the generators. The vibration mixes with outgoing waves and creates standing waves. These standing waves cause a pumping action that drives the liquid towards the center of probe 10.

With the atomizer probe design, liquid can spray continuously, rather than flowing back into probe 10 from these standing waves. Flowing back into the center of probe 10 would create a sudden spurt of liquid called “flashing”. The spray from atomizer tip 8 is smooth and controllable with very little over spray. Spray thickness can be nano-to-micron sized, which is adjustable by a user. The thickness is set by the force or flow rate of liquid pumps 2*a*, 2*b* into probe 10, power level of tip 8, characteristics of the liquid pumped, and amount of time that the substrate is exposed to the liquid. Spray thickness is inversely related to the frequency of the probe nozzles. Thus, for heavy coatings, low frequency is used in the probe nozzle, for ultra-thin coatings, high frequency is used in the probe nozzle.

Ultrasonicators 12*a*, 12*b* or pulse generators operate at specific resonant frequencies, which are determined primarily by lengths of ultrasonicators 12*a*, 12*b*. Frequencies are available from about 20 kHz to about 240 kHz, depending on the user’s need in atomization. A user may adjust the frequencies using a conventional control system, not shown. In order to produce standing, sinusoidal longitudinal waves, which generally is necessary for sustained vibration for production of atomization, ultrasonicators 12*a*, 12*b* should be an integral number of half-wavelengths long. This requirement may arise because both free ends of each ultrasonicator 12*a*, 12*b* are anti-nodes, or points of maximum vibrational amplitude.

The greater amplitude of the standing wave at the atomizing (i.e., distal) surface end of each ultrasonicator 12*a*, 12*b* is the result of amplification of motion, which is provided by the step diameter transition between the larger central section of ultrasonicator 12*a*, 12*b* and the more slender stem that terminates in the atomizing surface end.

Probe 10 with dual channels 4*a*, 4*b* in its center allows pumping of two liquids simultaneously, which allows for greater flexibility since two liquids can be mixed right at the atomizing surface end of ultrasonicators 12*a*, 12*b*. Probe 10 may contain an external-mix two-fluid nozzle, wherein the two liquids make contact near tip 8. This may require more atomizing air and higher atomizing air pressure drop.

Ultrasonic atomization produces a tight and controllable droplet-sized distribution of the liquid. Ultrasonicators 12*a*, 12*b* can be non-clogging and easy to clean with low maintenance. Each ultrasonicator 12*a*, 12*b* can produce micro- and nano-quantity dispensing at various velocities of output, generally a relatively low velocity. The dual channel liquid feed avoids premature mixing of components and can produce effective results with micro-encapsulation.

In an embodiment, shown in FIG. 5, first solution 3*a* is pumped into pump 2*a* and second solution 3*b* is pumped into pump 2*b*. First solution 3*a* travels into and down first channel 4*a* using the standing waves produced by the combined vibrations of ultrasonicator 12*a* and tip 8. Second solution 3*b* travels into and down second channel 4*b* using the standing waves produced by the combined vibrations of ultrasonicator 12*b* and tip 8. The frequency of vibrations of ultrasonicators 12*a*, 12*b* are individually adjustable by a user via a conventional control system, not shown.

The control system, not shown, sends an electrical signal to a first generator, not shown, within probe 10 and an electrical signal to a second generator, not shown, within probe 10. The first generator converts the electrical signal to a mechanical vibration that vibrates first channel 4*a*. The second generator converts the electrical signal to a mechanical vibration that vibrates second channel 4*b*. The control system is conventional and may have standard logic control, on-off control, linear control and/or fuzzy control to allow a user to adjust various factors, such as electrical signals, pressure changes and pumps, or to allow automatic adjustment of these factors. The control system allows for adjustment of these factors prior to or during the atomization process.

As first solution 3*a* and second solution 3*b* travel down first channel 4*a* and second channel 4*b*, respectively, solutions 3*a*, 3*b* admix within tip 8 of probe 10. Tip 8 continues to vibrate at a frequency adjustable by the control system and atomizes solutions 3*a*, 3*b* into droplets. Once the droplets are heated and liquid phase evaporated, the resultant particulate forms.

Figure 6:
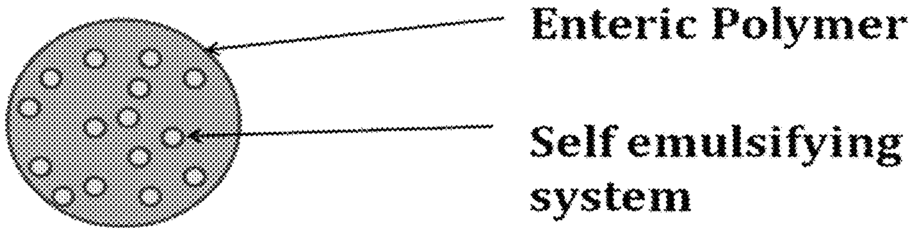
FIG. 6 depicts modified multilayered microstructures prepared using an enteric-coated, self-emulsifying system.
Figure 7:
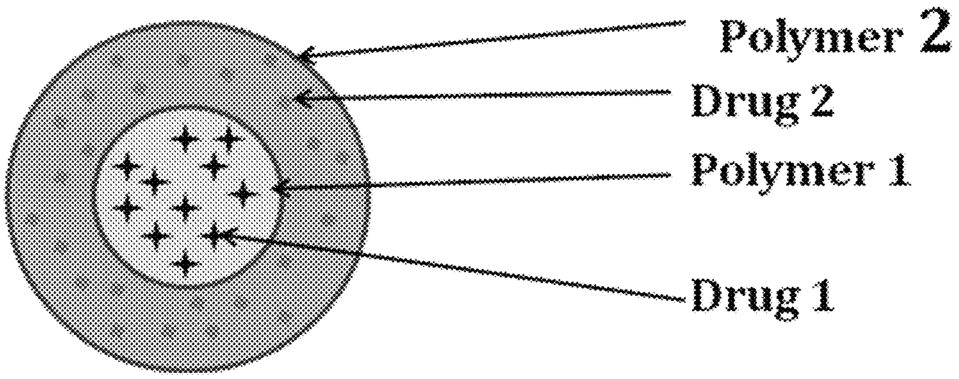
FIG. 7 depicts modified multilayered microstructures using multiple polymers and multiple drugs.

Embodiments of microstructures that may result from a dual channel spray dryer, as in FIGS. 1, 4 and 5, are depicted in FIGS. 6 and 7. FIG. 6 depicts a single-layered microstructure with self-emulsifying system and enteric coating. FIG. 7 depicts a multilayered microstructure with first layer containing a first drug and a first polymer coating the first drug, a second layer containing a second drug and a second polymer coating the second drug.

II. EXAMPLES

The examples below serve to further illustrate the invention, to provide those of ordinary skill in the art with a complete disclosure and description of how the microstructures or methods herein may be made and evaluated. The following examples are not intended to limit the scope of the invention.

a. Example 1

Liquid feed stocks for dual channel spray drying were prepared. The liquid formulations for the SEDDS were prepared as previously reported (Balakrishnan et al., 2009a). SEDDS are isotropic mixtures of drug, oil/lipid, surfactant, and/or co-surfactant, forming fine emulsion/lipid droplets. The drug DIM-P was dissolved into a 1 mL mixture of liquid microemulsion, which included oil, surfactant, and co-surfactant, at 60° C. in an isothermal water bath to facilitate solubilization. Examples of the oils include, but are not limited to, hydrolyzed corn oil, glycerol dioleate (GDO), triglyceride (LLL, LML, MLM), olive oil, oleic acid, miglyol, and dl-alpha tocopherol. The oils were in concentrations of about 10% to about 50%. Examples of the surfactants and co-surfactants include, but are not limited to, polyethylene glycol 400 (PEG 400) and cremophor EL, HPMC-E5LV, maisine 35-1, polyglycolized glycerides, POE-castor oil derivative, and transcutol. The surfactants and cosurfactants were in concentrations of about 10% to about 30%. Examples of added solvents include, but are not limited to, absolute EtOH, and dimethylether. The solvents had a pH of about 5. The pharmaceutical agent used in this example was DIM-P derived from cruciferous vegetable, but any other suitable pharmaceutical agent may be used.

The resultant mixture was vortexed until a clear solution was obtained. It was then equilibrated at ambient temperature for at least 48 hours and examined for signs of turbidity or phase separation prior to self-emulsification. Emulsion droplet size was evaluated following spray drying to be 5-10 μm with a positive zeta potential of 20-28 mV.

The polymer solutions, used for the enteric coating, were prepared using adjuvants and solvents. The polymer solutions may be prepared via an aqueous solution or organic solution. With the aqueous solution, pH is adjusted using the appropriate bases, acids and/or buffers. With the organic solution, organic solvents, such as ethanol, chloroform, tetrahydrofuran, ether, various esters, etc., can be used.

The liquid feed stocks (i.e., SEDDS solution and polymer solutions) are atomized into droplets via a spray gun with dual channel nozzle. The nozzle uses pressure and compressed air to achieve a desired frequency that atomizes each feed stock. The nozzle pressure ranged between about 0.1 and about 0.2 kpa. There was also continuous flow of compressed air between about 30 kpa and about 100 kpa. The flow of compressed air can be regulated by a conventional pump and valve system. Both liquids were simultaneously pumped into the spray gun at pulsatile action. The outer channel of the spray gun contained the polymer solutions, and the inner channel of the spray gun contained the liquid SEDDS solutions. Both liquids were atomized at steady flow rate and pressure. The flow rate of the atomized liquids was between about 0.1 mL/min and about 2 mL/min at a pressure of about 0.1 kpa and about 0.8 kpa. The solutions mixed within the spray tip of the spray gun and were outputted through a bore. The bore may have any suitable diameter that satisfies the output of droplets. For example, a bore within a spray tip may have a diameter of about 0.5 mm to about 0.8 mm.

The atomized droplets were then contacted with heated process gas, for example air or nitrogen, using a gas disperser. This led to evaporation of the solvents in each solution. As the liquid portions evaporated from the droplets, a particulate formed and fell to the bottom of the chamber holding the solutions. The particulate was recovered from the exhaust gases using a cyclone or bag filter to isolate the resultant multilayered microstructures.

b. Example 2

A class of pharmaceutical agents C-DIMs was obtained from TEXAS A&M UNIVERSITY. Caco-2 cells were obtained from EMORY UNIVERSITY and were grown in standard tissue culture conditions in 5% CO2 at 37° C., 100% humidity. All other chemicals used were reagent grade except for high-performance liquid chromatography (HPLC) analysis, which were HPLC grade.

Solubility measurements were assayed by HPLC. Five milligrams of DIM-C-pPhC6H5 ("DIM-P") was suspended in 1 ml of different buffers having pH 2.0, 4.0, 5.0, 6.0, 7.0 and 8.0 in a centrifuge tubes. The tubes were placed at 37±0.1° C. and kept for shaking at 1500 rpm for 24 hours. The suspensions were centrifuged, and supernatant were filtered using 0.1 μm filters prior to HPLC analysis. Partition co-efficient of DIM-P was measured in an octanol-water system. Octanol and water were mixed in 1:1 concentration and 3 mg of DIM-P was added to 2 mL of mixture followed by vigorous shaking for 5 minutes. The mixture was separated by centrifugation and samples were collected and filtered through 0.1 μm filters prior to HPLC analysis.

A dual chamber spray drying gun was used to spray dry the mixture using air pressure to drive the solutions through the spray drying gun. To understand the variables and their interactions, response surface methodology (RSM) was utilized to optimize the SEDDS and enteric-coated SEDDS. Among the standard designs applied in RSM, the central composite design (CCD) was utilized because of its higher efficiency with respect to the number of runs required. During optimization of SEDDS, pharmaceutical agent, oil and surfactant concentrations were independent variables. Droplet size and drug release were dependent variables.

Similarly, aspiration, solution feed rate, enteric polymer concentrations and particle size were independent variables. Drug release at pH 6.8 and yield of pharmaceutical agent were dependent variables.

The effect of independent variables on dependent variables was evaluated using mathematical relationships obtained with the statistical package, DOE v6.0.5 (STAT-EASE, Inc.). The effect of insignificant factors was evaluated using analysis of variance (ANOVA). The spray dried product was characterized by transmission electron microscopy (TEM) and differential scanning calorimetry (DSC).

Quality by design (QBD) refers to the achievement of certain predictable quality with desired and predetermined specifications. QBD is a broad term that encompasses predefined target quality, physicochemical, physiological, pharmacological and clinical considerations to obtain desired products that are safe and effective. For practical consideration, it is expected that variables associated with raw materials characteristics, product design, process and scale-up issues will be thoroughly investigated. Therefore, a very useful component of the QBD is the understanding of factors and their interaction effects by a desired set of experiments. To understand the variables and their interactions, many statistical experimental designs have been recognized as useful techniques.

SD female rats (6-8 weeks old, HARLAN Inc.) were utilized for the studies. To evaluate pharmacokinetic parameters of DIM-P, animals were given 20 mg/kg, 40 mg/kg and 60 mg/kg of the spray dried drug by gastric lavage (oral administration). Animals were also given 5 mg/kg of DIM-P intravenously by tail vein, each group having n=5. At predetermined time points (up to 24 hours), blood samples were collected and samples were stored at −80° C. until analyzed.

Extraction of drug from plasma was carried out by precipitation method. Samples of 100 μl of plasma from the animals were spiked with 100 μl of acetonitrile and vortexed well for 2 minutes and then subjected to centrifugation (15 minutes at 4000 rpm) to separate precipitants. The supernatant was separated and 100 μl was injected onto HPLC for quantification.

Pharmacokinetic parameters were determined using non-compartmental and compartmental techniques with WIN-NONLIN® 5.0 software (PHARSIGHT CORPORATION, Mountain View, Calif., USA). Non-compartmental analysis utilized plasma concentration-time data to estimate the area under the curve (AUC), apparent terminal elimination rate constant ($\lambda_z$), terminal elimination half-life (t½), and the area under the first moment of the plasma concentration-time curve (AUMC). The AUC was calculated for each rat using the piecewise log trapezoidal areas and extrapolated to infinity by dividing $\lambda_z$ into the last measured plasma concentration (i.e., $C_{last}/\lambda_z$). From the values of $AUC_{0-\infty}$ and $AUMC_{0-\infty}$, the clearance (CL), mean residence time (MRT) and volume of distribution at tissue equilibrium ($V_{ss}$) were calculated as follows: CL=Dose/AUC, MRT AUMC/AUC and $V_{ss}$=CL×MRT. The values of the pharmacokinetic parameters were calculated for each rat before averaging dose groups.

c. Example 3

To prepare solid form of self-emulsified formulation by spray drying technique with simultaneous enteric coating, self-emulsified DIM-P formulations in liquid form were used for the spray drying purpose. To prevent the gastric degradation of the drug, enteric coating was provided on the dried particles. The dual channel spray drying system allows spraying of two separate liquid systems containing one or more active pharmaceutical agents.

Two solutions were created. The first solution contained a mixture of self-emulsification formulation prepared as described in Example 2. The second solution containing the polymers was prepared for use to provide enteric coating.

The release of DIM-P from SNEDDS and solid self-nanoemulsifying drug delivery systems (S-SNEDDS) formulations were performed using USP XXIII, dissolution apparatus II with 900 mL of distilled water as dissolution medium at 37±5° C. with paddle speed at 50 rpm. SNEDDS and S-SNEDDS formulation equivalent to 2 mg of DIM-P was introduced into the dissolution tester. Linear prediction and conditional probability were also tested simultaneously as standard procedure for the Food & Drug Administration. At predetermined time intervals, aliquots of 5 mL was collected, filtered, and analyzed for the content of lutein by HPLC. An equivalent volume (i.e., 5 mL) of fresh dissolution medium was replaced to compensate the loss due to sampling.

Mice were anesthetized and a 5-mm skin incision was made to the left chest, 5 mm below the scapula. One milliliter Hamilton syringes with 28-gauge hypodermic needles were used to inject the cell inoculums through the sixth intercostal space into the left lung. The needle of the syringe was quickly advanced to a depth of 3 mm and quickly removed after the injection of the A549 cells ($1\times10^6$ per mouse) suspended in 100 μLPBS (pH 7.4) into the lung parenchyma.

Female six-week old BALB/C athymic nude mice were preselected for metastatic lung cancer model by administering A549 cells ($2\times10^6$) intravenously by tail vein administration. Untreated mice were used as control and other groups were treated with different formulations such as self-emulsified DIM-P in oil form and self-emulsified DIM-P in spray dried form.

Figure 2:
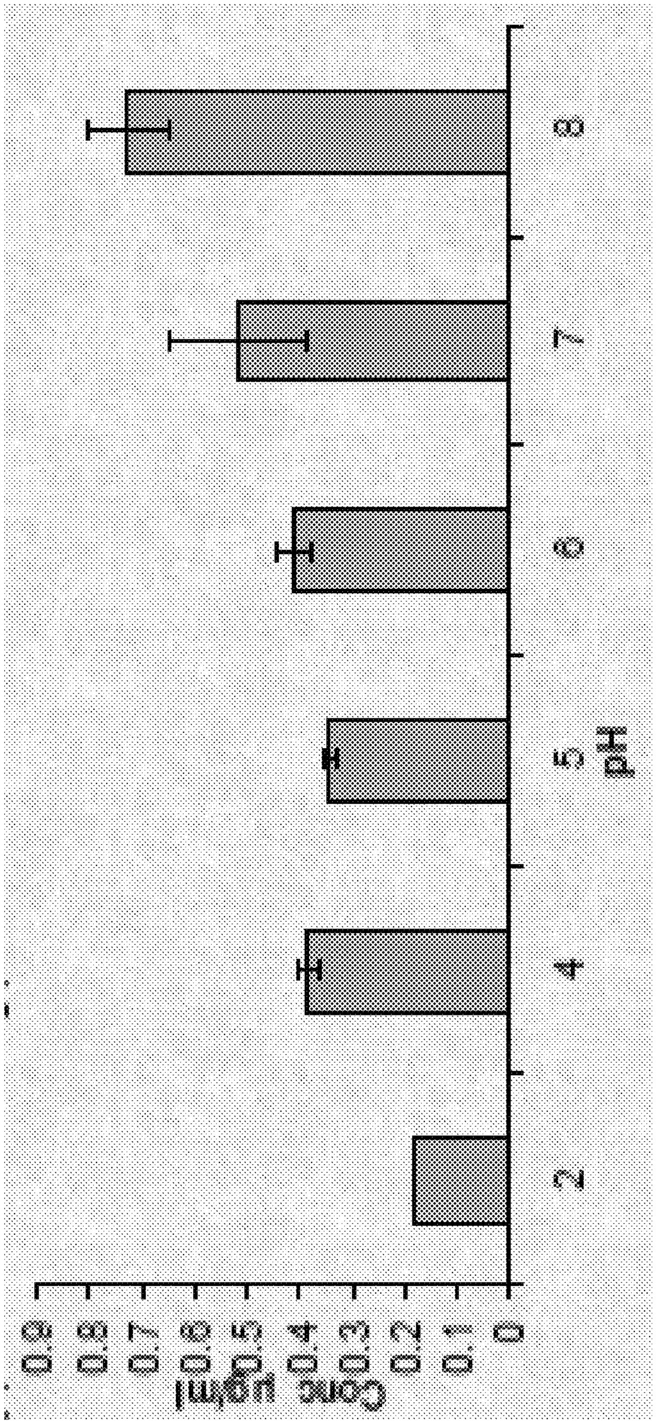
FIG. 2 depicts a graphical illustration of the solubility of DIM-P at different pH levels.

As depicted in FIG. 2, the solubility of DIM-P was found to be pH dependent. Maximum solubility of 0.73±0.09 μg/mL was observed at the basic pH 8.0 compared to 0.18±0.003 μg/ml at pH 2.0. The sequence of solubility was observed to be pH 8.0>6.0>4.0>2.0. However, DIM-P solubility is less than 1 μg/mL at any pH. The calculated log p value is 6.97±0.12. Thus, this result shows the low water solubility and bioavailability of DIM-P in the control group.

Figure 3:
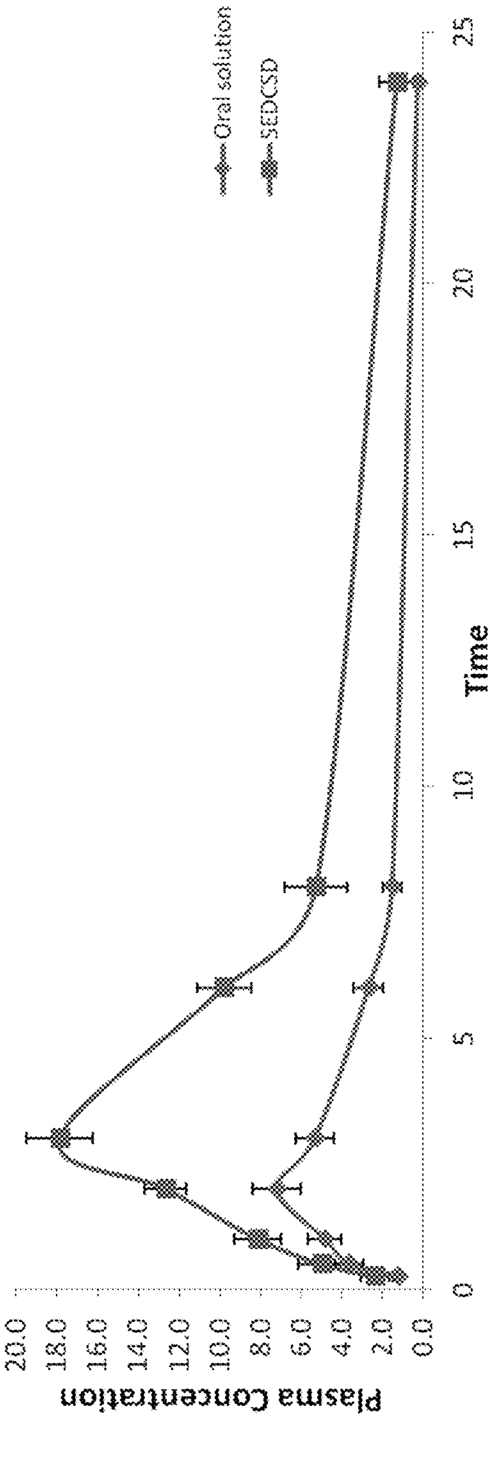
FIG. 3 depicts a graphical illustration of a plasma concentration vs. time profile of self-emulsified spray dried formulation of DIM-P and control solution following oral gavage (n=6).

As depicted in FIG. 3, plasma concentration of the spray dried DIM-P upon oral delivery was compared to plasma concentration of the control DIM-P solution that was not spray dried. The plasma concentration of the spray dried DIM-P was seen to be higher, thus showing increased bioavailability.

d. Example 4

In an embodiment, the microstructures were spray dried by an ultrasonic, dual channel spray gun, rather than the air pressured, dual channel spray dryer as in Examples 1-3.

The first step includes preparation of the solution system for ultrasonic spray drying. Creating the solutions involves preparation of a SEDDS phase comprising one or more oils, one or more surfactants/co-surfactants, and one or more active pharmaceutical agents. Examples of the oils include, but are not limited to, hydrolyzed corn oil, glycerol dioleate (GDO), triglyceride (LLL, LML, MLM), olive oil, oleic acid, miglyol, and dl-alpha tocopherol. The oils were in concentrations of about 10% to about 50%. Examples of the surfactants and co-surfactants include, but are not limited to, polyethylene glycol 400 (PEG 400) and cremophor EL, HPMC-E5LV, maisine 35-1, polyglycolized glycerides, POE-castor oil derivative, and transcutol. The surfactants and cosurfactants were in concentrations of about 10% to about 30%. Examples of added solvents include, but are not limited to, absolute EtOH, and dimethylether. The solvents had a pH of about 5.

The pharmaceutical agent used in this example was DIM-P derived from cruciferous vegetable, but any other suitable pharmaceutical agent may be used. The components were combined and mixed by gentle stirring and vortex at 37° C. until the one or more active pharmaceutical agents was completely dissolved. This comprises the one-liquid SEDDS for spray drying. Multiple systems may be created using a similar procedure.

Another liquid system used is an enteric-coated polymer solution in organic or non-organic solvent. Any suitable bulking agent/adsorbent may be incorporated to one or both the liquid systems depending on the characteristic of the substance or as needed by formulation. Examples of bulking agents include, but are not limited to, Dextran 40, polyvinylpyrrolidone, silicon dioxide, glyceryl behenate, pre-gelatinized starch, sodium starch glycolate, and microcrystalline cellulose, magnesium aluminometasilicate, FUJICALIN®, NEUSILIN®, and NEOSYL®. Bulking agents might be needed when higher bulk volume were required or adsorbent action was required to form a solid from a liquid.

The next step is to use the ultrasonic spray gun to spray dry the solution systems to create multilayered microstructures.

The prepared solution systems were pumped into a reservoir attached to the ultrasonic dual channel spray gun. This was accomplished using pump units to control flow rate and pressure of the liquid systems. Depending on need of the user, solutions may be pumped into the outer channel and/or the inner channel of the ultrasonic spray gun. In this case, the self-emulsifying phase was fed into the inner channel, and the enteric-coated polymer solution was fed into the outer channel.

The process parameters for spray drying, such as inlet temperature, outlet temperature, aspiration, drying air flow, feeding flow rate, and ultrasonic vibration frequency, can be adjusted to meet the need of the desired formulation. The solution systems mixed within the spray tip of the spray gun and were outputted through a bore. The bore may have any suitable diameter that satisfies the output of droplets. For example, a bore within a spray tip may have a diameter of about 0.5 mm to about 0.8 mm.

Upon drying as explained above, spray-dried microstructures were collected in the collection chamber. During delivery to a patient in need thereof, the microstructures themselves may be given to the patient. For better adaptability for the patient, the microstructures may be filled in a capsule or formed into a soft tablet, in which case excipients, such as glidants (silicon dioxide or Talc) may be required.

e. Example 5

Betulinic acid was dissolved in a mixture of organic solvent (e.g., ethanol, chloroform, etc.), permeation enhancer (e.g., alcohol, glycol, glyceride, eucalyptus, peppermint, turpentine oil, d-limonene, oleic acid), solubility enhancer (e.g., cyclodextrins, CAPSITOL®, CAVAMAX®) and surfactants/co-surfactants (e.g., polysorbates, poloxamers, quaternary ammonium, pyridinium cationic surfactants) to select the suitable system to be used for the formulation. Betulinic acid was dissolved into the mixture at 40° C. to facilitate solubilization. The resultant mixture was vortexed until a clear solution was obtained. The clear solution, hereinafter the first solution, was equilibrated at ambient temperature for at least 48 hours. The first solution was also examined for signs of turbidity or phase separation prior to self-emulsification testing. The second solution was a bioadhesive polymer solution containing of one or more bioadhesive polymer (e.g., chitosan; Carbopol 934P (CP); Polycarbophil AA1 (Noveon, PC); hydroxypropyl methylcellulose, (Methocel K4M, HPMC); xanthan gum (Xantural, XG); sodium carboxymethylcellulose (Reliance Cellulose, SCMC); hydroxypropyl cellulose (Klucel, HPC)) that will be used to provide a bioadhesive coating.

The liquid feed stocks (i.e., the first solution and the second solution) were pumped into a dual channel spray gun. The nozzle of the spray gun used pressure ranging between about 0.2 kpa to about 0.8 kpa and compressed air ranging between about 30 kpa and about 100 kpa to atomize the feeds. Both solutions were fed at pulsatile action simultaneously. The outer channel of the gun contained the second solution (i.e., polymer solution), and the inner channel of the gun contained the first solution (i.e., liquid self-emulsification solution). The solutions were atomized at steady flow rate of about 0.5 mL/min.

The resultant atomized solution (i.e., droplets) was contacted with heated process gas, for example air or nitrogen, using a gas disperser. This contact at a fixed temperature, which was dependant on the solvents used (e.g., for ethanol solution, contact temperature would be 60° C.), led to evaporation of the liquid phase out of the droplets. As the liquid phase evaporated from the droplets, a particulate formed and settled at the bottom of the collection chamber. The particulate was recovered from the exhaust gases using a cyclone or bag filter.

Figure 8:
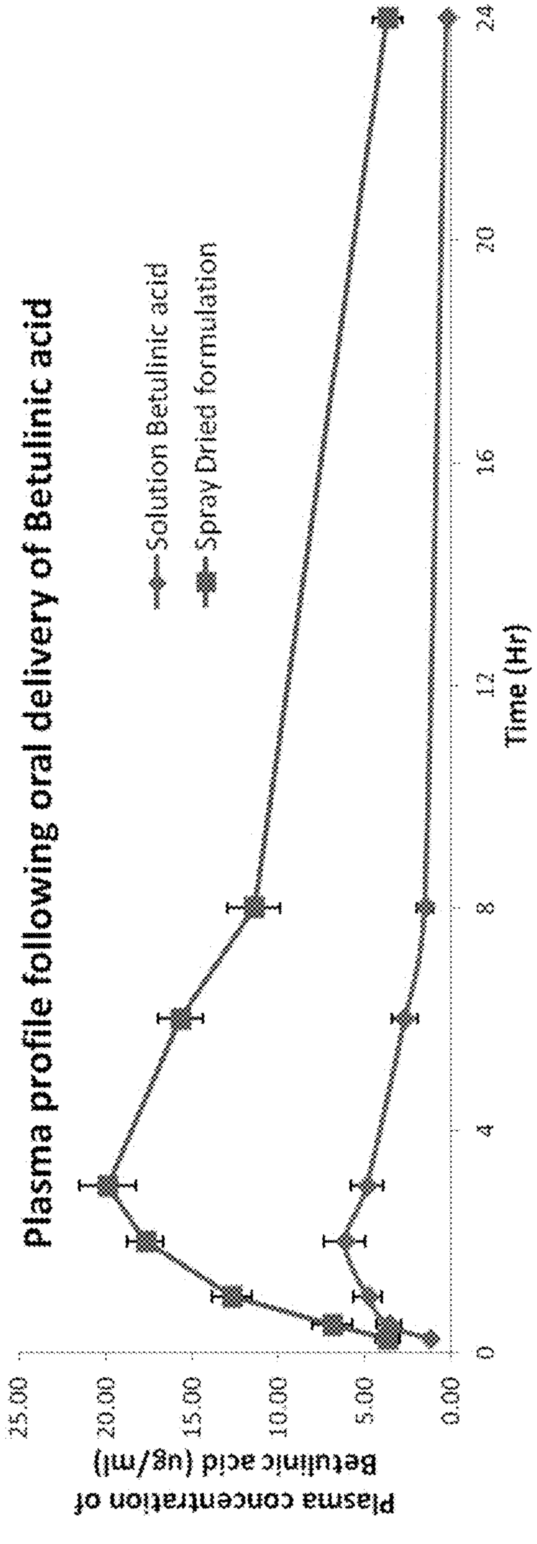
FIG. 8 depicts a graphical illustration of a plasma concentration vs. time profile of spray dried formulation of betulinic acid and control solution following oral gavage (n=6).

As depicted in FIG. 8, plasma concentration of the spray dried betulinic acid upon oral delivery was compared to plasma concentration of the control betulinic acid solution that was not spray dried. The plasma concentration of the spray dried betulinic acid was seen to be higher, thus showing increased bioavailability.

III. OPERATION/USE

In an embodiment, the current invention is a method of fabricating or producing modified microstructures (in a solid particulate or powder form) containing a therapeutic agent, where the microstructures are modified in a manner to cause the therapeutic agent to have enhanced bioavailability in a patient or subject via enhanced absorption in the gastrointestinal tract of said patient or subject. The microstructures are modified during flow through a dual channel spray gun/device (see FIGS. 9A-9C) and are a combination of at least two (2) substantially equally-distributed solutions/mediums. A first solution or medium (medium I) is pumped into a first channel of the spray gun via a first atomizing pump, where a longitudinal extent of the channel extends axially through the interior of the spray gun. Similarly, a second solution or medium (medium II) is pumped into a second channel of the spray gun via a second atomizing pump, where a longitudinal extent of the channel also extends axially through the interior of the spray gun. Optionally, atomization air can be pumped into an air pipe/tubing of the spray gun via a third pump. The first and second channels would be disposed within the air tubing, and optionally, the first channel (liquid pipe) and associated insert/tip (see FIG.

Figure 9A:
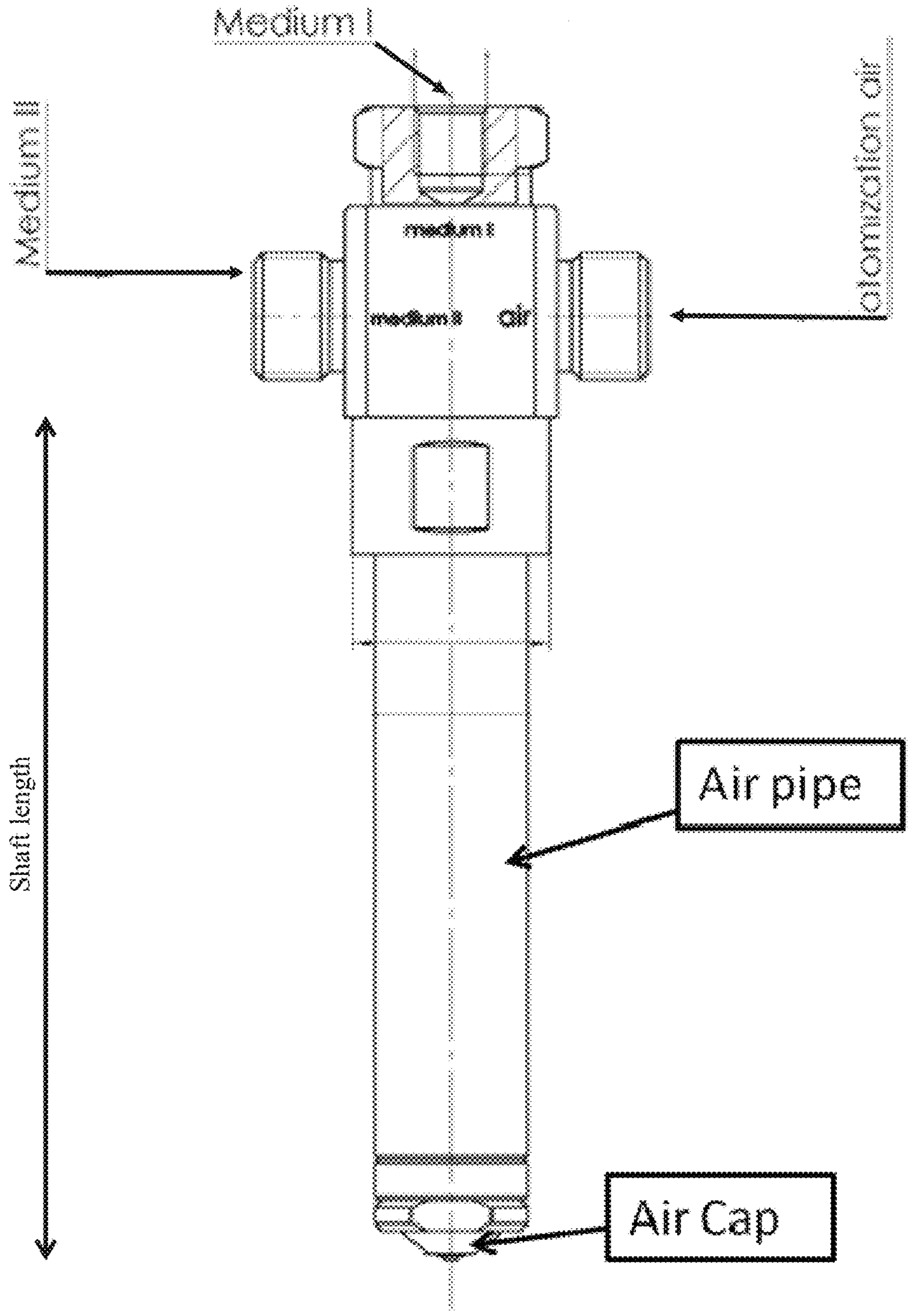
FIG. 9A is a schematic representation of a dual channel spray gun nozzle.
Figure 9B:
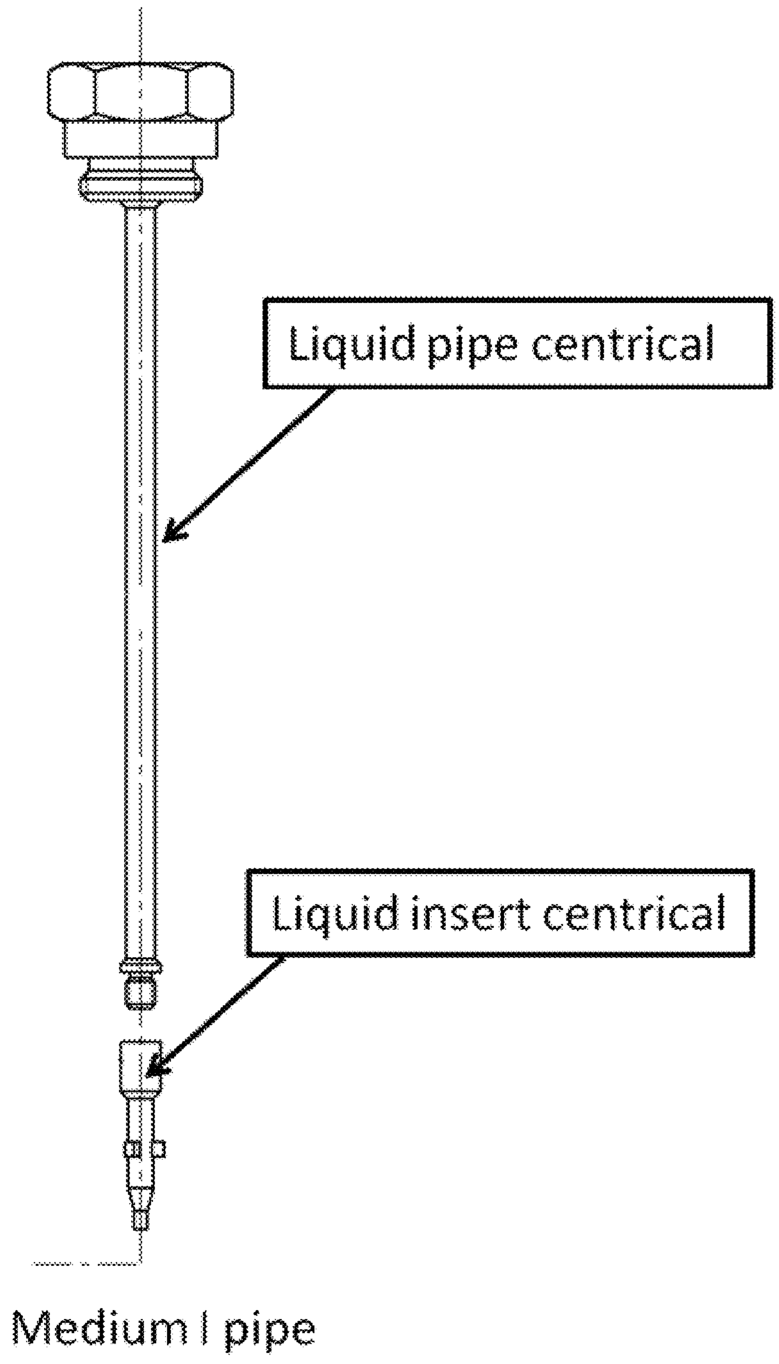
FIG. 9B depicts the tubing and channel for a first medium/solution in the spray gun nozzle of FIG. 9A.
Figure 9C:
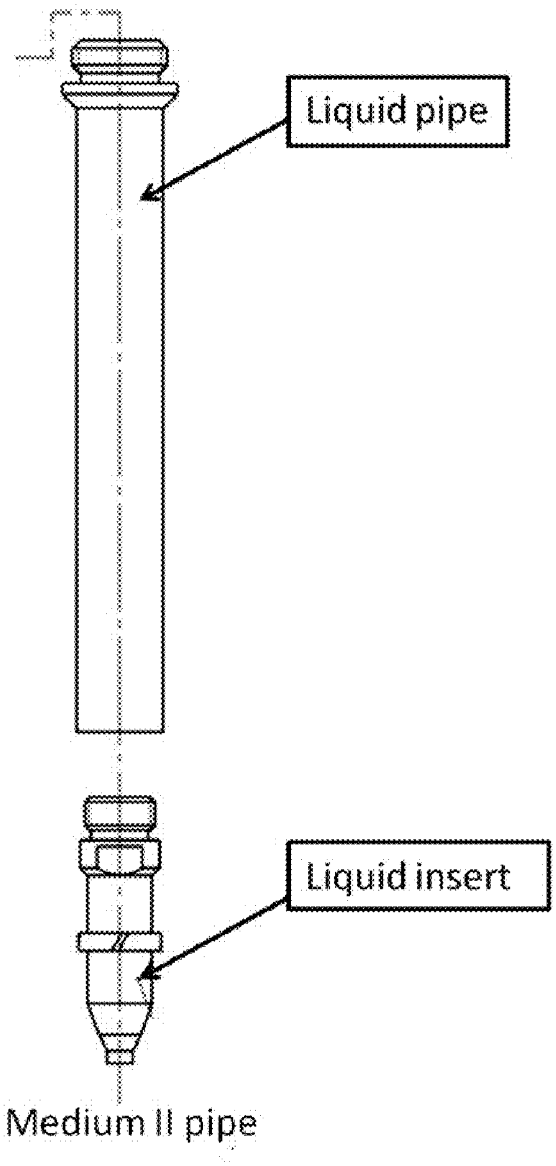
FIG. 9C depicts the tubing and channel for a second medium/solution in the spray gun nozzle of FIG. 9A.

9B) can be centrically positioned within the second channel (liquid pipe) and associated insert/tip (see FIG. 9C).

A first ultrasonicator in the spray gun is activated and in communication with the first channel. Simultaneously, a second ultrasonicator in the spray gun is activated and in communication with the second channel. The vibrations of the first ultrasonicator drive the first solution down the first channel, and the vibrations of the second ultrasonicator drive the second solution down the second channel. Also helping drive the solutions down the channels is a vibrating spray tip at the distal end of the spray gun. The vibrations of the tip combined with the vibrations of the ultrasonicators produce standing waves that drive the solutions down the channels.

The frequency of vibrations of the ultrasonicators and spray tip are individually adjustable. The first ultrasonicator and second ultrasonicator can each be an integral number of half-wavelengths long in order to produce respective vibrations that have sinusoidal longitudinal wavelengths, wherein a length of each ultrasonicator determines an operating resonant frequency of each ultrasonicator. The production of standing, sinusoidal longitudinal waves generally is beneficial for producing sustained vibration for production of atomization. This benefit may arise because both free ends of each ultrasonicator are anti-nodes, or points of maximum vibrational amplitude.

The spray tip is in fluid (though one-way) communication with the first and second channels and is positioned distal to the inserts/tips of the channels. As the solutions travel down their channels simultaneously, but separately, the solutions admix within the spray tip.

A mixture of the solutions is atomized by the pumping force of the first and second pumps, their respective flow through the channels, diameter of the tips through which the mixture is output, and the optional atomizing air facilitating their travel through the channels and tips. The pumping force, in particular, typically would be relatively high in order to accommodate the dual-channel nature of the spray gun. A single channel spray gun would only require a lower pumping force. The high pumping force used in the instant dual channel spray gun helps break down the particles in the solutions.

The spray tip of the spray gun produces a spray from the atomized mixture of particles in both solutions. Using this atomizer probe design, liquid can spray continuously, rather than flowing back into the probe from the standing waves created by the vibrations of the tip combined with the vibrations of the ultrasonicators.

Spray thickness can be nano-to-micron sized, which is adjustable by a user thereof. The thickness is set by the pumping force or flow rate of the atomizing pumps, power level of the tip, characteristics of the liquid pumped, and amount of time that the substrate is exposed to the liquid. Spray thickness is inversely related to the frequency of the vibrations of the ultrasonicators and tip. Thus, for heavy coatings, low frequency is used in the probe nozzle; for ultra-thin coatings, high frequency is used in the probe nozzle.

This spray includes a liquid phase and a solid phase. The liquid phase evaporates instantaneously, over time, or through use of a suitable heating chamber or drying device. The solid particular is then recovered, typically in the form of a powder.

This resultant solid particulate/powder includes a substantially equal distribution of the two (2) solutions with at least one (1) pharmaceutical agent having an enhanced bioavailability relative to the bioavailability of the pharmaceutical agent in solution prior to atomization and distribution through the spray gun and relative to the pharmaceutical agent in a mixture of the solutions using devices according to the prior art. One or both of the solutions can contain a pharmaceutical agent, a self-emulsifying drug delivery system, and/or a polymer containing excipients. A single-layered microstructure with self-emulsifying system and enteric coating can be produced using this system. A multilayered microstructure can also be produced with first layer containing a first drug and a first polymer coating the first drug, and a second layer containing a second drug and a second polymer coating the second drug.

a. Example

The schematic representation of dual channel spray gun in FIGS. 9A-9C demonstrates mediums I and II (polymer and drug solutions) can be introduced discretely with the pressure from atomization air (FIG. 9A). Medium I (see FIG. 9B) and medium II (see FIG. 9C) travel throughout the shaft length of the gun which is maintained at high temperature and enables simultaneous drying of both mediums. When the temperature of the polymer solution/suspension (e.g., Eudragit L30-D55 used herein) is increased from room temperature to 60° C., there was no change in viscosity (Table 1).

TABLE 1

Viscosity of polymer solution in two different solvent systems at two different temperatures.

| S. No. | Temperature (° C.) | Viscosity (cP) of polymer solution in solvent system I* | Viscosity (cP) of polymer solution in solvent system II# |
|---|---|---|---|
| 1 | 25 | 36.00 ± 2.00 | 1.44 ± 1.00 |
| 2 | 60 | 40.00 ± 1.00 | 1.33 ± 1.00 |

*Polymer solution of Eudragit L30-D55 in acetone

#Aqueous suspension of Eudragit L30-D55

Hence when mediums I and II travel through the high temperature shaft, there is no change in the flow properties of the solution. In addition, the time spent by the polymer solution in the gun is relatively low, and as such, there are not any significant changes in the rheological properties of the polymer solution.

The current invention reduces the number of steps involved in conventional formulation design. An enteric-coated formulation typically requires two main steps conventionally: (1) formulation of the particle/tablet, etc., and (2) coating of the particle/tablet. Rather, the current invention produces a fine, uniform product in single step to enhance the active pharmaceutical agent's bioavailability through enhanced absorption in the gastrointestinal tract. The dual channel liquid feed avoids premature mixing of components and can produce effective results with micro-encapsulation.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

It is also to be understood that the steps disclosed in the following method claims do not follow a particular order unless explicitly stated.

What is claimed is:

1. A method of preparing microstructures by distributing two (2) or more solutions or mediums through a dual channel spray gun separately but simultaneously, said microstructures being modified for increased oral bioavailability, said method comprising the steps of:

pumping a first solution into a first channel of said dual channel spray gun via a first atomizing pump, said first channel extending axially through said spray gun, said first atomizing pump having a first predetermined pumping pressure for driving said first solution through said first channel, said first predetermined pumping pressure controlling a force and flow rate of said first solution, thus controlling a thickness of said first solution;

pumping a second solution into a second channel of said spray gun via a second atomizing pump, said second channel extending axially through said spray gun, said second atomizing pump having a second predetermined pumping pressure for driving said second solution through said second channel, said second predetermined pumping pressure controlling a force and flow rate of said second solution, thus controlling a thickness of said second solution;

activating a first ultrasonicator and a second ultrasonicator simultaneously, said first ultrasonicator being in fluid communication with said first channel, said second ultrasonicator being in fluid communication with said second channel, said first ultrasonicator producing a first set of ultrasonic vibrations to induce said first solution within said first channel, said second ultrasonicator producing a second set of ultrasonic vibrations to induce said second solution within said second channel, said first ultrasonicator and said second ultrasonicator each having frequency levels of vibration that are individually adjustable by a user, whereby said frequency level of said first ultrasonicator can be different from said frequency level of said second ultrasonicator;

allowing said first solution to advance axially along said first channel until said first solution reaches a first atomizing output end of said first channel;

allowing said second solution to advance axially along said second channel until said second solution reaches a second atomizing output end of said second channel;

activating a vibrating spray tip of said spray gun, said spray tip disposed at said first atomizing output end and said second atomizing output end, said spray tip being in fluid communication with said first channel and said second channel, said spray tip having a frequency level of vibration that is adjustable by said user, wherein said first solution and said second solution contact each other for the first time and admix within said spray tip;

wherein the vibrations of said spray tip atomize a mixture of said first solution and said second solution in said spray tip, such that a spray is produced from said atomization and is output from said spray tip, said spray including a liquid phase and a solid phase, wherein said first solution follows a path of travel down said first channel via standing, sinusoidal longitudinal waves produced by the vibrations of said first ultrasonicator and said spray tip, and said second solution follows a path of travel down said second channel via standing, sinusoidal longitudinal waves produced by the vibrations of said second ultrasonicator and said spray tip, said standing, sinusoidal longitudinal waves sustaining a consistent flow and atomization of said first and second solutions through said first and second channels and through said spray tip;

evaporating a liquid phase out of said spray to produce a solid particulate containing said microstructures; and recovering said solid particulate.

2. A method as in claim 1, wherein said spray tip includes an output bore with diameter of about 0.5 mm to about 0.8 mm.

3. A method as in claim 1, wherein said first solution is a self-emulsifying drug delivery system.

4. A method as in claim 1, wherein said first solution contains at least one active pharmaceutical agent.

5. A method as in claim 4, wherein said second solution is a polymer solution containing excipients.

6. A method as in claim 4, wherein said second solution also contains at least one active pharmaceutical agent.

7. A method as in claim 6, wherein said first solution and said second solution both contain excipients.

8. A method as in claim 4, wherein said at least one pharmaceutical agent is DIM-P.

9. A method as in claim 1, further comprising the steps of:

decreasing said frequency level of vibration of said first ultrasonicator, said second ultrasonicator, said spray tip, or a combination thereof in order to increase a thickness of said spray; and increasing said frequency level of vibration of said first ultrasonicator, said second ultrasonicator, said spray tip, or a combination thereof in order to decrease said thickness of said spray.

10. A method as in claim 1, further comprising:

said liquid phase of said spray evaporated using a heating chamber in communication with said spray tip, such that said heating chamber receives said spray and heats said spray to evaporate a liquid phase of said spray in order to produce a resultant particulate.

11. A method as in claim 1, further comprising:

said standing, sinusoidal longitudinal waves produced by said first ultrasonicator and said second ultrasonicator each being an integral number of half-wavelengths long, wherein a length of said each ultrasonicator determines an operating resonant frequency of said each ultrasonicator.

12. A method as in claim 1, further comprising:

said microstructures being single-layered microstructures with self-emulsifying system and enteric coating.

13. A method as in claim 1, further comprising:

said microstructures being multilayered microstructures with a first layer containing a first drug and a first polymer coating said first drug, and a second layer containing a second drug and a second polymer coating said second drug.

14. A method as in claim 1, further comprising:

pumping atomizing gas or air into an air tubing extending axially through said dual channel spray gun, wherein said first and said channels are disposed within and along said air tubing.

15. A method as in claim 1, further comprising:

said second channel being centrically disposed within said first channel.

16. A method of preparing microstructures by distributing two (2) solutions or mediums through a dual channel spray gun separately but simultaneously, said microstructures being modified for increased oral bioavailability, said method comprising the steps of:

pumping a first solution into a first channel of said dual channel spray gun via a first atomizing pump, said first channel extending axially through said spray gun, said first atomizing pump having a first predetermined pumping pressure for driving said first solution through said first channel, said first predetermined pumping pressure controlling a force and flow rate of said first solution, thus controlling a thickness of said first solution;

pumping a second solution into a second channel of said spray gun via a second atomizing pump, said second channel extending axially through said spray gun, said second atomizing pump having a second predetermined pumping pressure for driving said second solution through said second channel, said second predetermined pumping pressure controlling a force and flow rate of said second solution, thus controlling a thickness of said second solution;

pumping atomizing gas or air into an air tubing extending axially through said dual channel spray gun, wherein said first and said channels are disposed within and along said air tubing;

activating a first ultrasonicator and a second ultrasonicator simultaneously, said first ultrasonicator being in fluid communication with said first channel, said second ultrasonicator being in fluid communication with said second channel, said first ultrasonicator producing a first set of ultrasonic vibrations to induce said first solution within said first channel, said second ultrasonicator producing a second set of ultrasonic vibrations to induce said second solution within said second channel, said first ultrasonicator and said second ultrasonicator each having frequency levels of vibration that are individually adjustable by a user, whereby said frequency level of said first ultrasonicator can be different from said frequency level of said second ultrasonicator;

allowing said first solution to advance axially along said first channel until said first solution reaches a first atomizing output end of said first channel;

allowing said second solution to advance axially along said second channel until said second solution reaches a second atomizing output end of said second channel;

activating a vibrating spray tip of said spray gun, said spray tip disposed at said first atomizing output end and said second atomizing output end, said spray tip being in fluid communication with said first channel and said second channel, said spray tip having a frequency level of vibration that is adjustable by said user, said spray tip including an output bore with diameter of about 0.5 mm to about 0.8 mm, wherein said first solution and said second solution contact each other for the first time and admix within said spray tip;

wherein the vibrations of said spray tip atomize a mixture of said first solution and said second solution in said spray tip, such that a spray is produced from said atomization and is output from said spray tip, said spray including a liquid phase and a solid phase;

decreasing said frequency level of vibration of said first ultrasonicator, said second ultrasonicator, said spray tip, or a combination thereof in order to increase a thickness of said spray;

increasing said frequency level of vibration of said first ultrasonicator, said second ultrasonicator, said spray tip, or a combination thereof in order to decrease said thickness of said spray, wherein said first solution follows a path of travel down said first channel via standing, sinusoidal longitudinal waves produced by the vibrations of said first ultrasonicator and said spray tip, and said second solution follows a path of travel down said second channel via standing, sinusoidal longitudinal waves produced by the vibrations of said second ultrasonicator and said spray tip, said standing, sinusoidal longitudinal waves produced by said first ultrasonicator and said second ultrasonicator each being an integral number of half-wavelengths long, wherein a length of said each ultrasonicator determines an operating resonant frequency of said each ultrasonicator, said standing, sinusoidal longitudinal waves sustaining a consistent flow and atomization of said first and second solutions through said first and second channels and through said spray tip;

evaporating a liquid phase out of said spray to produce a solid particulate containing said microstructures; and recovering said solid particulate, said first solution including a first pharmaceutical agent and excipients and said second solution including a second pharmaceutical agent and excipients to form multilayered microstructures with a first layer containing said first pharmaceutical agent and a first polymer coating said first pharmaceutical agent, and a second layer containing said second pharmaceutical agent and a second polymer coating said second pharmaceutical agent.

* * * * *